United States Patent [19]

Nanjyo et al.

[11] Patent Number: 5,438,262
[45] Date of Patent: Aug. 1, 1995

[54] METHOD AND APPARATUS FOR THE NONDESTRUCTIVE DETERMINATION OF TORSIONAL BREAKAGE TORQUE OF TUBULAR CARBON FIBER REINFORCED COMPOSITE MATERIALS

[75] Inventors: Atsushi Nanjyo; Akiyoshi Kojima, both of Yokohama, Japan

[73] Assignee: Nippon Oil Co. Limited, Tokyo, Japan

[21] Appl. No.: 88,526

[22] Filed: Jul. 9, 1993

[30] Foreign Application Priority Data

Jul. 10, 1992 [JP] Japan .................................. 4-184169

[51] Int. Cl.⁶ ....................... G01N 27/90; G01R 33/12
[52] U.S. Cl. ....................... 324/238; 324/209; 324/225; 324/232; 324/242; 324/262
[58] Field of Search ............... 324/202, 209, 225, 227, 324/229, 230, 232-234, 236-243, 262

[56] References Cited

U.S. PATENT DOCUMENTS

| | | | |
|---|---|---|---|
| 2,065,118 | 12/1936 | Davis, Jr. | 324/241 |
| 2,418,686 | 4/1947 | Zuschlag | 324/240 X |
| 3,132,299 | 5/1964 | Hochschild | 324/238 |
| 4,488,114 | 12/1984 | David et al. | 324/241 X |
| 4,556,846 | 12/1985 | D'Hondt | 324/238 |

FOREIGN PATENT DOCUMENTS

5-107231 4/1993 Japan .

*Primary Examiner*—Gerard R. Strecker
*Attorney, Agent, or Firm*—Finnegan, Henderson, Farabow, Garrett & Dunner

[57] ABSTRACT

In order to improve product quality control through quantitative determination of a defect and quantitative judgement of the quality of a product, an alternating current is applied to a standard product coil into which is inserted a standard object, and to a test object coil into which is inserted a test object, and eddy currents are measured by means of a bridge circuit. If the test object coil is at a location removed from a flaw, the bridge circuit output voltage is zero, while if the test object coil is at the location of the flaw, a predetermined voltage is output. A determination of torsional breakage torque of the shaft inspection is carried out by correcting the output voltage for dependence on the cross sectional area ratio of the test object relating to the cross sectional area of the coil and for the influence of flaw size depending on the location.

13 Claims, 17 Drawing Sheets

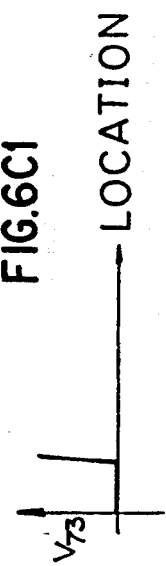
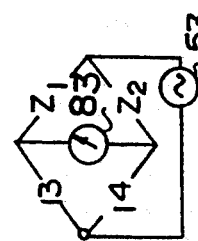
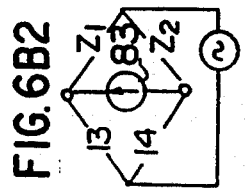
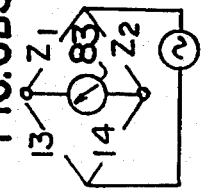
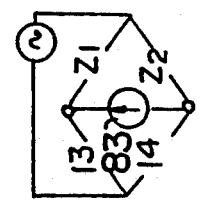
FIG.6A1  FIG.6A2  FIG.6A3  FIG.6A4
FIG.6B1  FIG.6B2  FIG.6B3  FIG.6B4
FIG.6C1  FIG.6C2  FIG.6C3  FIG.6C4

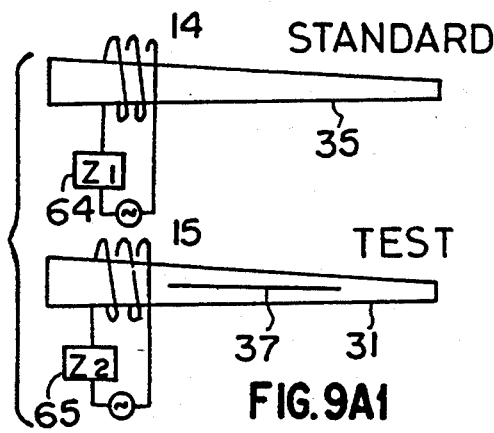
FIG. 9A1
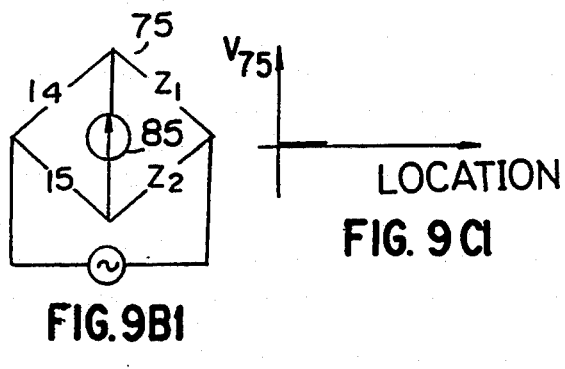
FIG. 9B1
FIG. 9C1
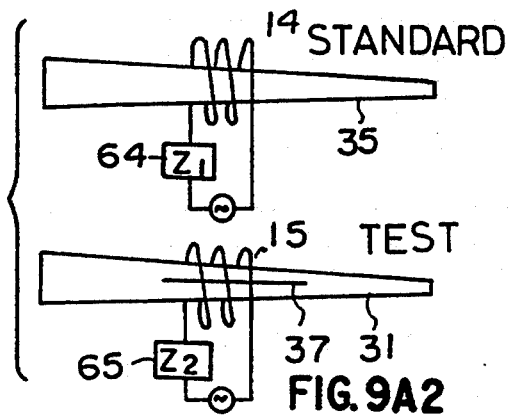
FIG. 9A2
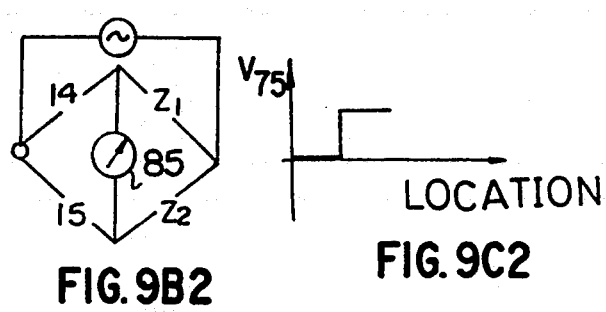
FIG. 9B2
FIG. 9C2
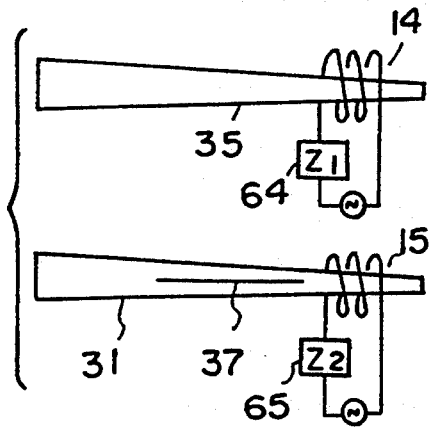
FIG. 9A3
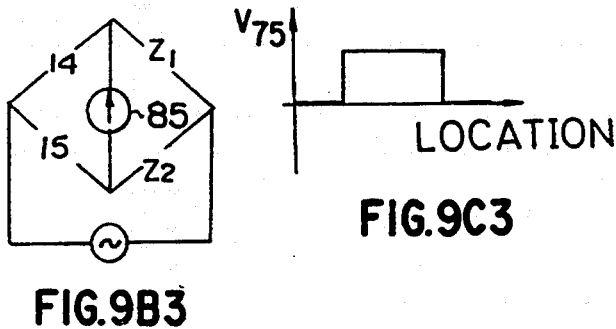
FIG. 9B3
FIG. 9C3

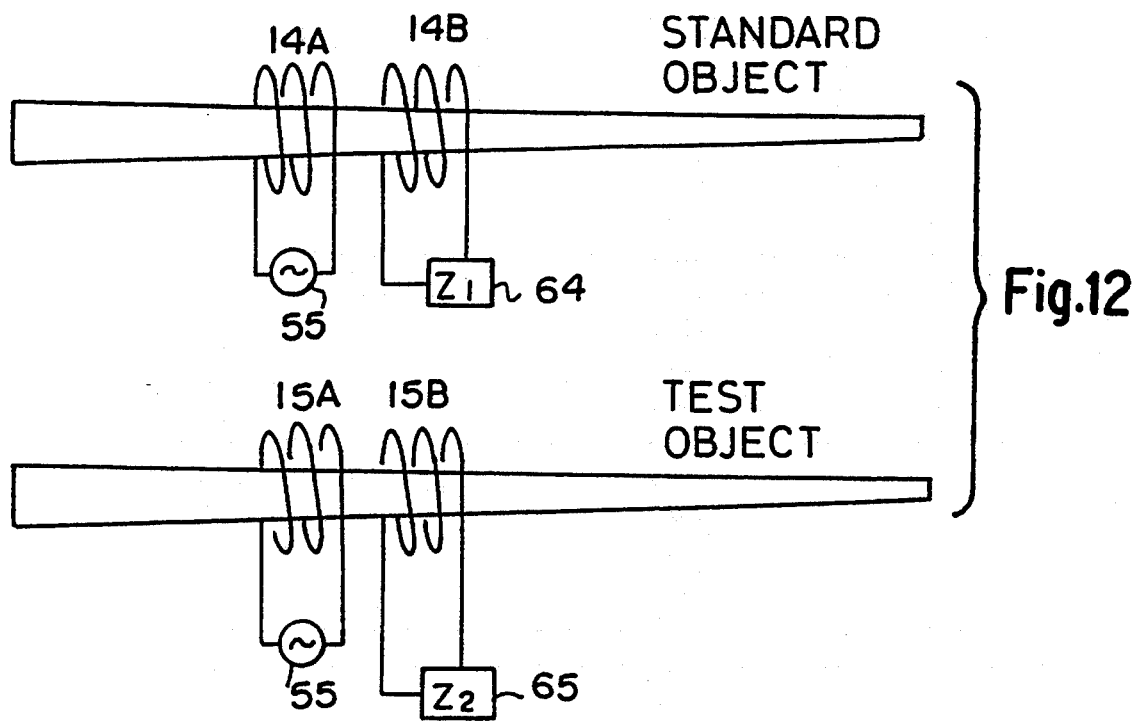
Fig.12
Fig.13
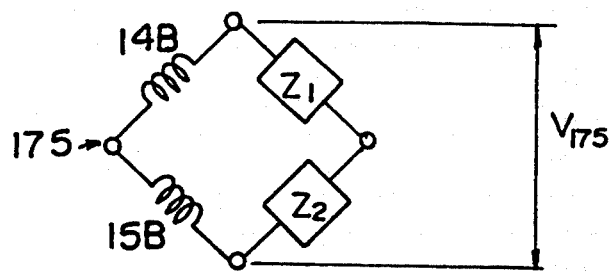

METHOD AND APPARATUS FOR THE NONDESTRUCTIVE DETERMINATION OF TORSIONAL BREAKAGE TORQUE OF TUBULAR CARBON FIBER REINFORCED COMPOSITE MATERIALS

BACKGROUND OF THE INVENTION

1. Field of the Invention

The present invention relates to method and apparatus for the nondestructive determination of torsional breakage torque of tubular carbon fiber reinforced composite materials (referred to subsequently as tubular CFRC materials), such as, for example, the inspection of a CFRC material shaft at the time of fitting to a golf club to determine whether or not defects exist in the shaft. The present invention also relates to method and apparatus that can be used in the quality control of tubular CFRC materials, or products utilizing such materials.

2. Description of the Related Art

With carbon fiber, in particular with tubular composite materials utilizing carbon fiber which has a high elasticity, it is known that the physical properties of the tubular composite material can show a significant drop from the design value when defects such as broken strands occur as a result of faulty conditions at the time of manufacture.

These kinds of defect are likely to occur, particularly when manufacturing by the sheet lapping process, and in this case, it is generally not possible to detect the defect from the external appearance Consequently, conventional inspection methods involve those wherein the tubular composite material is destroyed and the failure strength measured. With these methods, since all of the test pieces are necessarily destroyed, it is not possible to test all products.

In view of the above, the present inventor previously filed a patent application (Japanese unexamined patent publication No. 5-107231) related to a defect detection method for tubular CFRC materials utilizing an eddy current flaw detection method.

Conventionally, eddy current flaw detection methods are widely used for the inspection of metal tubes. With these methods, output signals corresponding to defect locations such as locations A–E shown in FIG. 27, are obtained by comparing relative conditions between two adjacent points. Hence, signals $a_1$ to $e_1$ are output only at the starting point (suffix 1), and signals $a_2$ to $e_2$ are output only at the finishing point (suffix 2) of a flaw or defect. In the case of a continuous defect, an accurate assessment of the flaw condition is therefore not possible. This proves an obstacle to the improvement in inspection accuracy for tubular CFRC materials.

SUMMARY OF THE INVENTION

In view of the foregoing, it is an object of the present invention to provide a method for the nondestructive determination of torsional breakage torque of tubular CFRC materials which enables an accurate assessment of flaws when inspecting a tapered control of a product, through quantitative assessment of the flaws, and quantitative judgment of product quality. It is a further object of the present invention to provide an apparatus for nondestructive determination of torsional breakage torque of a tubular CFRC material which enables an improvement in quality control of the beforementioned product.

To achieve the above objective, the method for the nondestructive determination of torsional breakage torque of tubular CFRC materials according to the present invention involves a method for the nondestructive determination of torsional breakage torque of tubular carbon fiber reinforced composite materials comprising the steps of, inserting a tubular CFRC material test object and a standard object each into respective single or double coils, the standard object having the same external diametric dimensions as the test object and having a previously verified degree of flaws, passing a predetermined alternating current through each of the single or one of each of the double coils to generate eddy currents in the standard object and the test object, moving the coils relative to the standard object and the test object in an axial direction to scan the standard object and test object, detecting an output fluctuation of eddy currents due to a flaw as a bridge output voltage by means of each of the single coils or the coil other than the one coil of each of the double coils and a bridge circuit, wherein the test object and the standard object are of a tapered tubular carbon fiber reinforced composite material which has been wound with carbon fiber at a predetermined angle with respect to the axial direction, the output voltage is corrected on the basis of the diametric dimension at the scanning location of the test object, and the torsional breakage torque of the test object is quantitatively determined for each inspection location on the basis of the corrected output.

With the above method for the nondestructive determination of torsional breakage torque of tubular CFRC materials, the tubular CFRC material test object and the standard object which has the same external diametric dimensions as the test object, and has a previously verified degree of flaws, are inserted into the respective single or double coils.

Eddy currents are then generated in the standard object and the test object by passing a predetermined alternating current through each of the single or one of each of the double coils. A bridge circuit is formed by the single coil or the other of the double coils. If a flaw exists in the test object, an eddy current output fluctuation due to the flaw is detected as a bridge output voltage. Since the coils are moved in the axial direction relative to the standard object and the test object, the eddy current output is corrected on the basis of the diametric dimension at the scanning location of the test object, and the torsional breakage torque of the test object is quantitatively determined for each inspection location on the basis of the corrected output.

The apparatus according to the present invention, shown in FIG. 1 as a first technical means, involves an apparatus for the nondestructive determination of torsional breakage torque of tubular carbon fiber reinforced composite (CFRC) materials comprising a single or double standard object coil for accommodating a standard object which has the same external diametric dimensions as a tubular CFRC material test object and which has a previously verified degree of flaws, a single or double test object coil for accommodating the test object, an alternating current application means for passing an alternating current through each of the single or one of each of the double standard object and test object coils, a scanning means for moving the coil and the standard object and the test object relatively to each other in an axial direction, a bridge output voltage detection means for detecting, by means of each of the single or the other of each of the double standard object and test object coils and a bridge circuit, fluctuation of the eddy currents generated in the standard object and the test object by the alternating current application means due to a flaw, a correction means for correcting the output voltage on the basis of the diametric dimension at the scanning location of the test object and the standard object which are of a tapered tubular carbon fiber reinforced composite material which has been wound with carbon fiber at a predetermined angle with respect to the axial direction, and a torsional breakage torque determination means for quantitatively determining the torsional breakage torque of the test object on the basis of the output corrected.

With the above first technical means related to the apparatus for the nondestructive determination of torsional breakage torque of tapered tubular CFRC materials, the standard object which has the same external diametric dimensions as the tubular CFRC material test object, and which has a previously verified degree of flaws, is accommodated in the single or double standard object coil, and the test object is accommodated in the single or double test object coil.

The alternating current application device passes an alternating current through each of the single or one of each of the double standard object and test object coils, with the result that an alternating current magnetic field is generated inside and around the periphery of the coils. Since the standard object is placed in the single or double standard object coil, and the test object is placed in the single or double test object coil, an eddy current flows in the standard object and the test object, and if a flaw exists in the test object, the eddy current necessarily detours around this flaw resulting in a fluctuation in the eddy currents which are generated in the test object by means of the alternating current application device, is detected as a bridge output voltage by means of the single standard object coil and the single test object coil or the other coil of the double standard object coil and the other coil of the double test object coil and the bridge circuit.

The scanning device then scans by moving the coil and the standard object and the test object relatively to each other in an axial direction, while the correction device corrects the output voltage from the bridge output voltage detection device on the basis of the diametric dimension at the scanning location of the test object, thereby correcting for sensitivity related to diametric dimensions and influence of flaw size.

When detecting the eddy currents however, the detection sensitivity at the thin part of the shaft differs from that at the thick part. That is to say, if the test object cross sectional area relative to the coil cross sectional area is small then sensitivity is lowered.

Hence for a second technical means, the beforementioned correction device may comprise a cross sectional area ratio correction means which corrects the output of the bridge output voltage detection means on the basis of the cross sectional area ratio of the test object relative to the cross sectional area of the coil. Accordingly, with the second technical means, by correcting the output of the bridge output voltage detection device by means of the cross sectional area ratio correction device on the basis of the cross sectional area ratio of the test object relative to the coil cross sectional area (for example the inverse second power of the external diametric diameter or the inverse second power of the internal diametric dimension), then an output can be obtained from the bridge output voltage detection device which has been corrected for sensitivity related to the cross sectional area of the test object. The torsional breakage torque determination device then determines the torsional breakage torque of the test object based on the output fluctuation which has been thus corrected.

In addition, even for the same magnitude of strength, a difference in the flaw size and in the diameter at the location of the flaw affecting the strength gives a different influence on the torsional fracture torque (referred to subsequently as breakage torque). That is to say, even for the same sized flaw, its influence at a location of smaller diameter is larger.

Hence, for a third technical means, the beforementioned correction device may comprise a diameter correction means which corrects the output from the bridge output voltage detection means depending on the flaw size and the diameter at the inspection location of the flaw. Accordingly, with the third technical means, by correcting the output from the bridge output voltage detection device by means of the diameter correction device on the basis of the flaw size and the diameter at the location of the flaw (for example the difference of the inverse fourth power of the external diametric from the inverse fourth power of the internal diametric, then an output can be obtained from the bridge output voltage detection device which has been corrected for diameter related to the location of the flaw. The torsional breakage torque determination device then determines the torsional breakage torque of the test object on the basis of the output fluctuation which has been thus corrected.

For a fourth technical means, the beforementioned correction device may comprise the cross sectional area ratio correction device and a diameter correction device. Then an output can be obtained from the bridge output voltage detection device which has been corrected for sensitivity related to the cross section of the test object by means of the cross sectional area ratio correction device, and corrected for diameter related to the location of the flaw by means of the diameter correction device. The torsional breakage torque determination device then determines the torsional breakage torque of the test object strength on the basis of the output fluctuation which has been thus corrected.

Accordingly, with the present invention, accurate assessment of a flaw is possible, and since the flaw can be quantitatively assessed, accurate defect assessment also becomes possible so that defects can be quantitatively determined. Moreover, it is possible to instantaneously judge without any damage, whether or not the breakage torque of the test object exceeds or is below the pass standard value. Also, since the quality of the product may be determined quantitatively, the judgment system related to the quality judgment can be improved with the result that quality control of the products may be improved.

Other objects and aspects of the present invention will become apparent from the following description of the embodiment modes given in conjunction with the accompanying drawings.

BRIEF DESCRIPTION OF THE DRAWINGS

FIGS. 6A1, 6A2, 6A3, 6A4, 6B1, 6B2, 6B3, 6B4, 6C1, 6C2, 6C3 and 6C4 illustrate the relationship between the location of a defect and the output voltage for the first operating mode of the first embodiment.

FIGS. 9A1, 9A2, 9A3, 9B1, 9B2, 9B3, 9C1, 9C2 and 9C3 illustrate the relationship between the location of a defect and the output voltage for the second operating mode of the first embodiment.

FIG. 12 is a schematic diagram illustrating a second operating mode of the second embodiment of the present invention.

FIG. 13 is a bridge circuit diagram for the second operating mode of the second embodiment.

DETAILED DESCRIPTION OF THE INVENTION

A preferred embodiment of the present invention in the form of an apparatus for the nondestructive determination of torsional breakage torque for golf club shafts which are made of tubular CFRC material will be explained with reference to the drawings.

Figure 2:
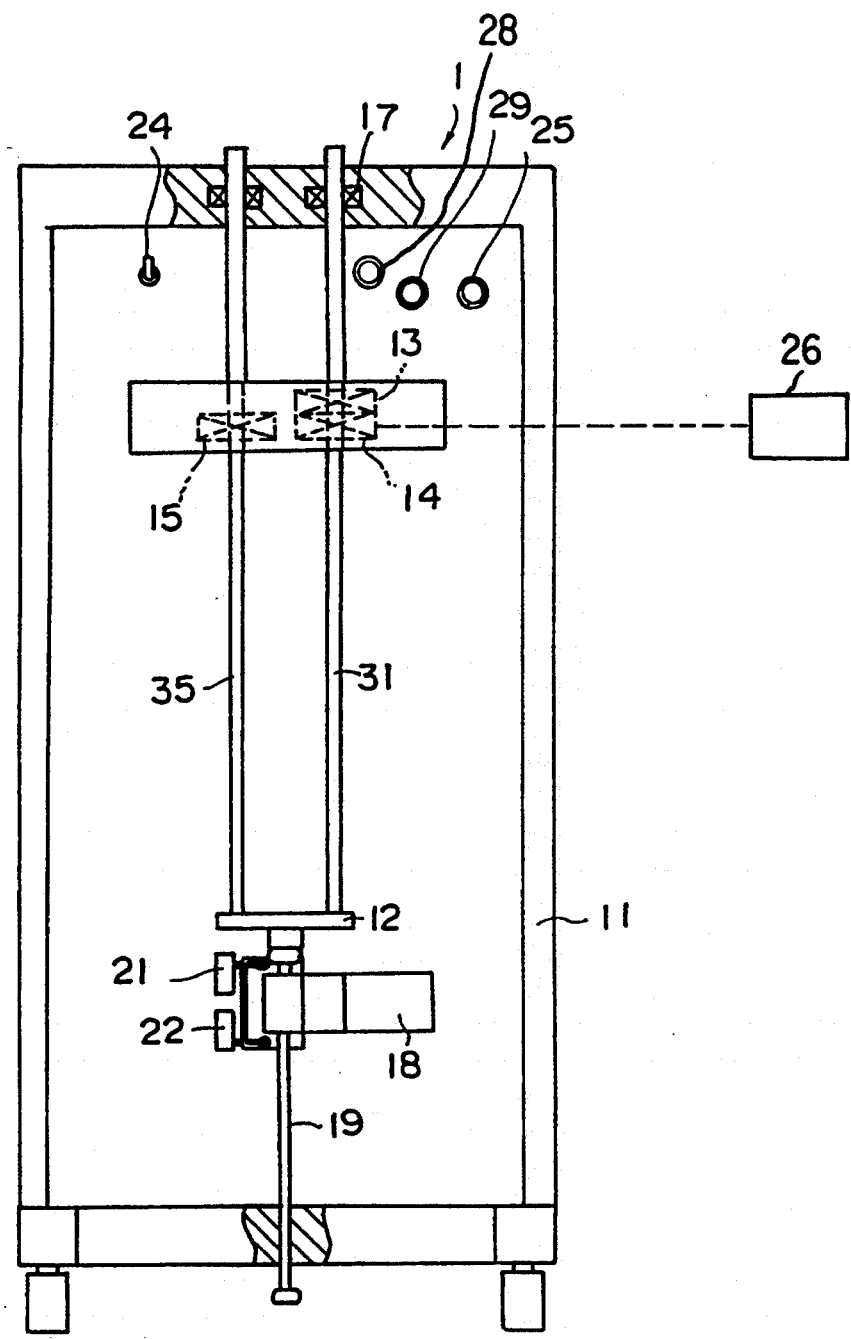
FIG. 2 is an elevation view illustrating a golf shaft test apparatus according to an embodiment of the present invention.

As shown in FIG. 2, a golf club shaft inspection apparatus 1 has a frame 11 on which is provided a mounting base 12 for mounting a golf club shaft 31 to be inspected (referred to as the test object in the following) and a standard golf club shaft 35 (referred to as the standard object in the following) adjacent to each other. The test object 31 which passes through a first coil 13 and a second coil 14, and the standard object 35 which passes through a third coil 15, are mounted with their axes in parallel. That is to say, the test object 31 and standard object 35 are installed so as to be symmetric about a position midway between them. The test object coil comprises the first coil 13 and the second coil 14, while the standard object coil comprises the third coil 15. Both the test object 31 and the standard object 35 are fixedly attached to the mounting base 12 so that the centers of both objects do not displace and free to slide in bearing 17. The test object 31 is supported so as to maintain a predetermined spacing with respect to the first coil 13 and second coil 14, while the standard object 35 is supported so as to maintain a predetermined spacing with respect to the third coil 15.

Figure 3:
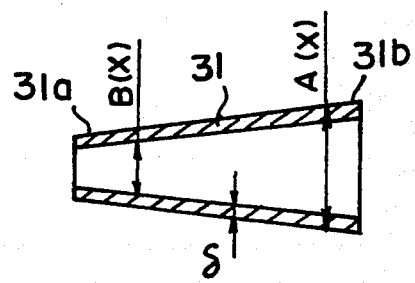
FIG. 3 is a sectional view of a test object of the embodiment of FIG. 2.

As shown in FIG. 3, the test object 31 is formed with a taper shape having a small bias layer outer diameter $A(x)$ at a tip end 31a and a large bias layer outer diameter $A(x)$ at a rear end 31b. The thickness $\delta$ of the bias layer is maintained uniform from the tip end 31a to the rear end 31b giving a hollow tubular construction with an inner diameter $B(x)$. The carbon fiber in the bias layer is wound at a predetermined angle with respect to the axial direction.

The standard object 35 is a golf club shaft with the same specifications as the test object 31 and precisely the same shape, and which has been prechecked to ensure that any flaws are extremely small in comparison to defects in the test object 31.

The mounting base 12 is scanned up and down in the axial direction by means of a ball screw 19 driven by a motor 18. Limit switches 21, 22 prescribe respective lower and upper scan limits of the mounting base 12. In effect, the scanning device comprises components such as the motor 18 and the ball screw 19.

Figure 4:
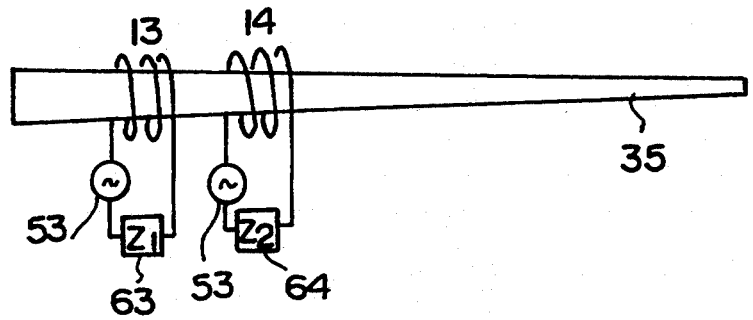
FIG. 4 is a schematic diagram illustrating a first operating mode of a first embodiment of the present invention.
Figure 7:
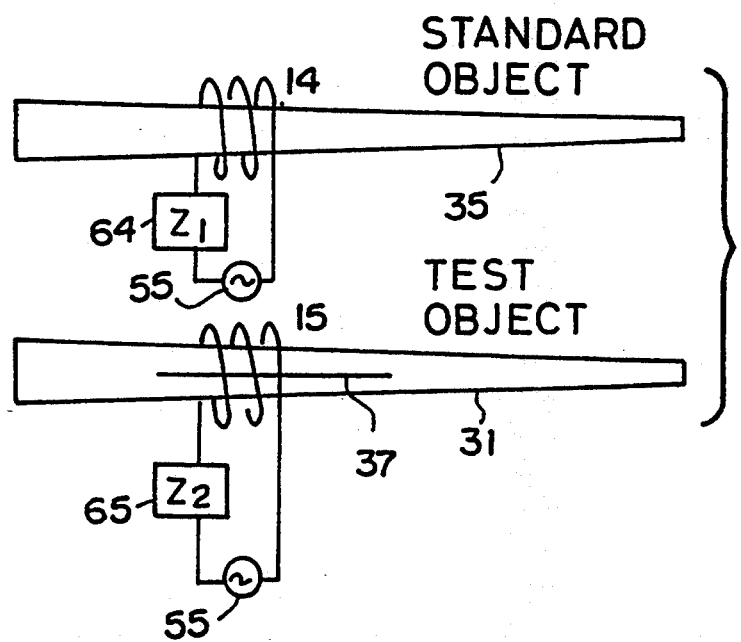
FIG. 7 is a schematic diagram illustrating a second operating mode of the first embodiment of the present invention.

A construction of a first embodiment according to the present invention is described as follows. The first coil 13, second coil 14, and third coil 15 comprise respective single coils 13, 14 and 15. As shown in FIG. 4, an alternating current source 53 is connected to the first coil 13 and second coil 14, or as shown in FIG. 7, an alternating current source 55 may be connected to the second coil 14 and third coil 15. The above connections may be switched by means of a self comparison/standard comparison switch 24 (FIG. 2). In effect, the beforementioned alternating current source makes up the alternating current application device.

An inspection start switch 25 (FIG. 2) is provided at the front face of the apparatus. By switching the start switch 25 ON, the scanning device operates so that the application of alternating current source for the self comparison/standard comparison and so on, and the detection of change in counter electromotive force are performed.

Also, an acceptance lamp 28 and a rejection lamp 29 are provided at the front face of the apparatus. The acceptance lamp 28 is lighted if the test object is judged to be accepted by the defect detection routine to be described later, while the rejection lamp 29 is lighted if the test object is judged to be rejected.

Further, a control unit 26 is the unit for controlling all the operations of the scanning device, the application of alternating current source for the self comparison/standard comparison and so on and the detection of change in counter electromotive force, or the torsional breakage torque determination device.

Initially, a first operating mode wherein only the first coil 13 and second coil 14 are used is described with reference to FIG. 4 and FIG. 5.

According to the first embodiment of the present invention, if the self comparison/standard comparison switch 24 is switched to the self comparison side, then the alternating current source is connected to the first coil 13 and the second coil 14 (FIG. 4), a bridge circuit 73 (FIG. 5) is formed so that the first coil 13 and the second coil 14 detect the change in counter electromotive force caused by a self induced current. On the other hand, if the self comparison/standard comparison switch 24 is switched to the standard comparison side, the alternating current source is connected to the second coil 14 and the third coil 15 (FIG. 7), and a bridge circuit 75 (FIG. 8) is formed so that the second coil 14 and the third coil 15 detect the change in counter electromotive force caused by the self induced current.

That is to say, in the first embodiment (FIG. 4), an alternating current source 53 and an impedance 63 are connected to the first coil 13, and the alternating current source 53 and an impedance 64 are connected to the second coil 14. At this time the switch 24 is switched to "self comparison".

Figure 5:
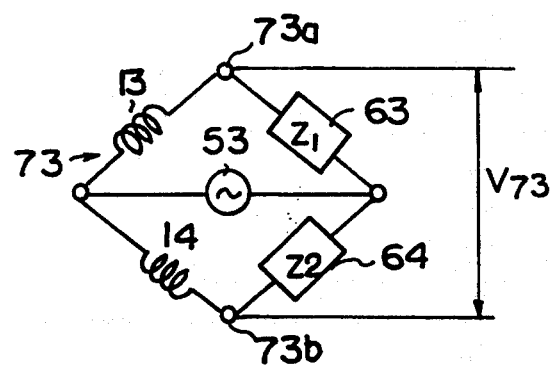
FIG. 5 is a bridge circuit diagram for the first operating mode of the first embodiment.

As shown in FIG. 5, the first coil 13 and second coil 14 are arranged to make up a bridge circuit 73 so as to detect a fluctuation in back EMF caused by self induced currents. With the insertion of a defective portion of a test object into the second coil 14 the balance of the bridge circuit 73 collapses giving an output voltage $V_{73}$ between terminals 73a and 73b, corresponding to the change in coil impedance of the second coil 14 due to the defect.

In the first operating mode the standard object 35 is used as a test object for inspection to determine the extent of defects such as a flaw 39 in the standard object 35.

The output conditions for the location of the flaw 39 in the standard object 35 and the output voltage $V_{73}$ are described as follows with reference to FIG. 6 for the case when the torsional breakage torque determination apparatus 1 according to the first embodiment is used in the first operating mode.

In FIG. 6, diagram 6A shows the positional relationship between the second coil 14 and the location of the flaw 39 when the first coil 13 and second coil 14 are scanned relative to the standard object 35. Diagram 6B shows circuit schematics with approximate needle positions for an output voltmeter 83 used to detect the output voltage $V_{73}$. Diagram 6C shows graphs indicating the output voltage $V_{73}$ detected by the output voltmeter 83.

Figure 1:
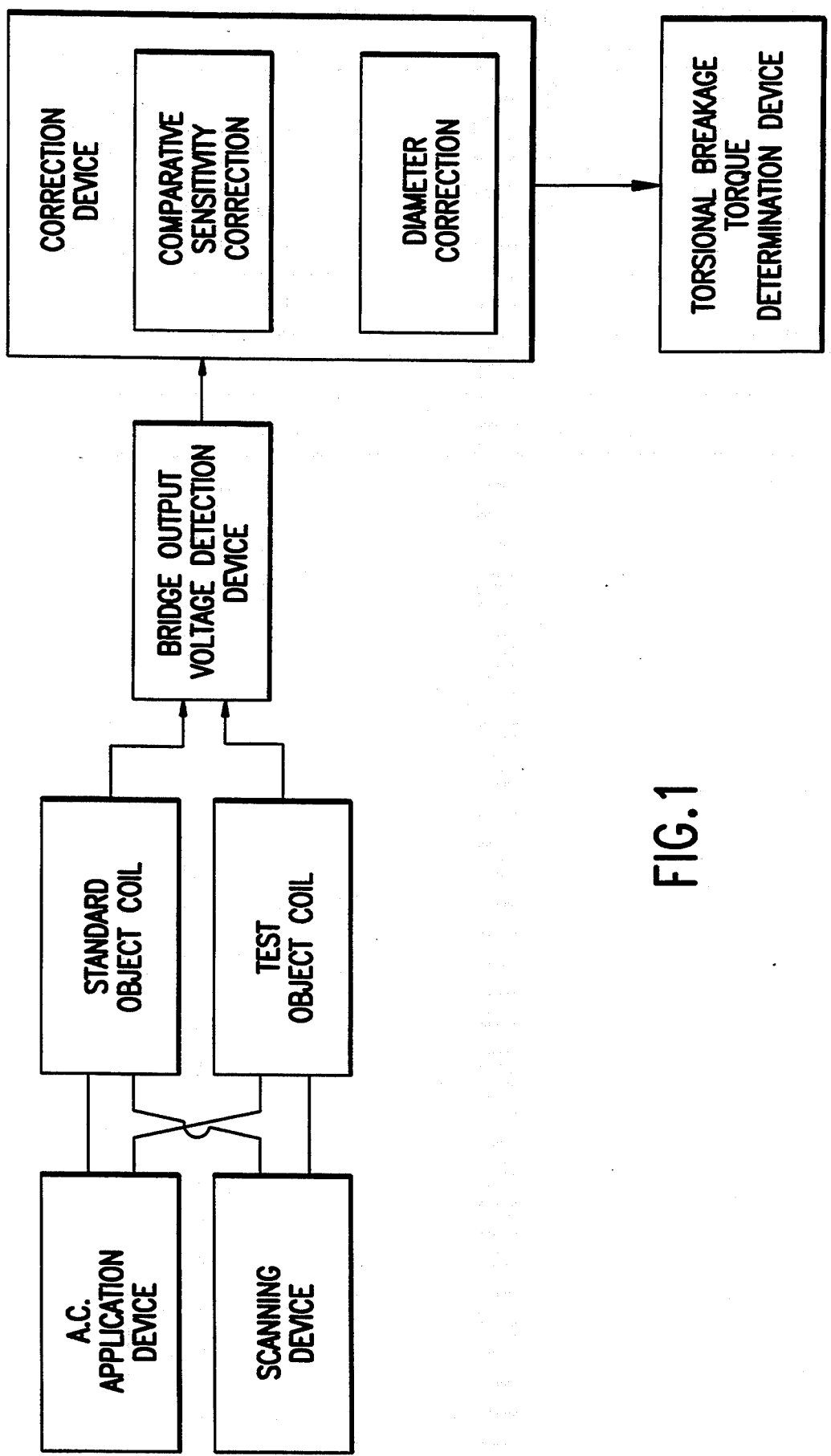
FIG. 1 is a block diagram showing a construction of the present invention.

In FIG. 6A1, the second coil 14 is at the location of the flaw 39, and as shown in FIG. 6C1, the output voltage $V_{73}$ peaks in the upward direction.

In FIG. 6A2, both the first coil 13 and second coil 14 are at the location of the flaw 39 so that the bridge circuit 73 is balanced. Consequently, as shown in FIG. 6C2, the output voltage $V_{73}$ goes to zero.

In FIG. 6A3, the first coil 13 is at the location of the flaw 39, and as shown in FIG. 6C3, the output voltage $V_{73}$ peaks in the downward direction.

In FIG. 6A4, both the first coil 13 and the second coil 14 are at a location removed from the flaw 39 so that the bridge circuit 73 is again balanced. Consequently, as shown in FIG. 6C4, the output voltage $V_{73}$ goes to zero.

Accordingly, with the first operating mode as described above, the extent of defects such as a flaw 39 in the standard object 35 can be investigated. However, with this mode, as with inspection methods that have heretofore been used, analysis is not possible when the flaw 39 exists as a plurality of flaws in layers in the test object 35.

Next, a second operating mode wherein only the second coil 14 and third coil 15 are used is described with reference to FIG. 7 and FIG. 8. In this case an alternating current source 55 and an impedance 64 are connected to the second coil 14, and the alternating current source 55 and an impedance 65 are connected to the third coil 15. At this time the switch 24 is switched to "standard comparison".

Figure 8:
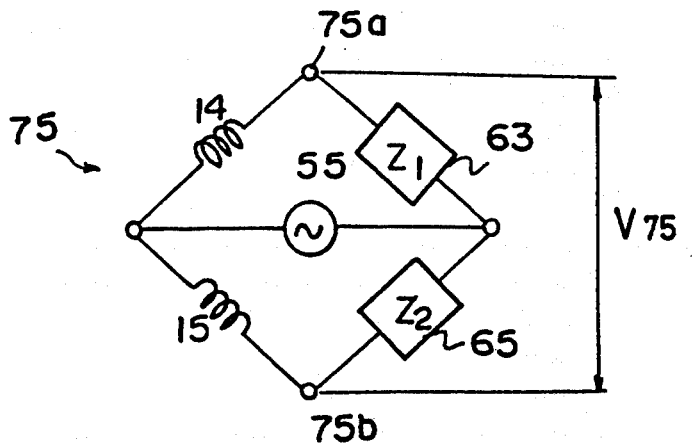
FIG. 8 is a bridge circuit diagram for the second operating mode of the first embodiment.

As shown in FIG. 8, the second coil 14 and third coil 15 are arranged to make up a bridge circuit 75 so as to detect a fluctuation in back EMF caused by self induced currents. With the insertion of a defective portion of a test object into the third coil 15, the balance of the bridge circuit 75 collapses giving an output voltage $V_{75}$ between terminals 75a and 75b, corresponding to the change in coil impedance of the third coil 15 due to the defect.

In the second operating mode the standard object 35 is inserted into the second coil 14, and the test object 31, as a trial object, is inserted into the third coil 15. The test object 31 is used for inspection to determine the extent of defects such as a flaw 37 compared to the standard object 35.

The output conditions for the location of the flaw 37 and the output voltage $V_{75}$ are described as follows with reference to FIG. 9 for the case when the apparatus 1 according to the first embodiment is used in the second operating mode.

In FIG. 9, diagram 9A shows the positional relationship between the third coil 15 and the location of the flaw 37 when the second coil 14 and third coil 15 are scanned relative to the standard object 35 and the test object 31. Diagram 9B shows circuit diagrams with approximate needle positions for an output voltmeter 85 used to detect the output voltage $V_{75}$. Diagram 9C shows diagrams indicating the output voltage $V_{75}$ detected by the output voltmeter 85.

In diagram 9A1, the third coil 15 is at a location removed from the flaw 37 so that the bridge circuit 75 is balanced. Consequently, as shown in diagram 9C1, the output voltage $V_{75}$ is zero.

In diagram 9A2, the third coil 15 is at the location of the flaw 37, and as shown in diagram 9C2, a predetermined output voltage $V_{75}$ peaks in the upward direction.

In diagram 9A3, the third coil 15 is at a location removed from the flaw 37 so that the bridge circuit 75 is again balanced. Consequently, as shown in diagram 9C3, the output voltage $V_{75}$ goes to zero.

Accordingly, with the second operating mode as described above, the test object 31 can be inspected to determine the extent of defects such as a flaw 37 compared to the standard object 35. The second operating mode thus functions in effect according to the first embodiment of the present invention. That is to say, the bridge output voltage detection device comprises the bridge circuit 73 and the bridge circuit 75.

Next, a construction of a second embodiment according to the present invention is described, with components the same as those in the first embodiment indicated by the same symbols and description omitted.

Figure 10:
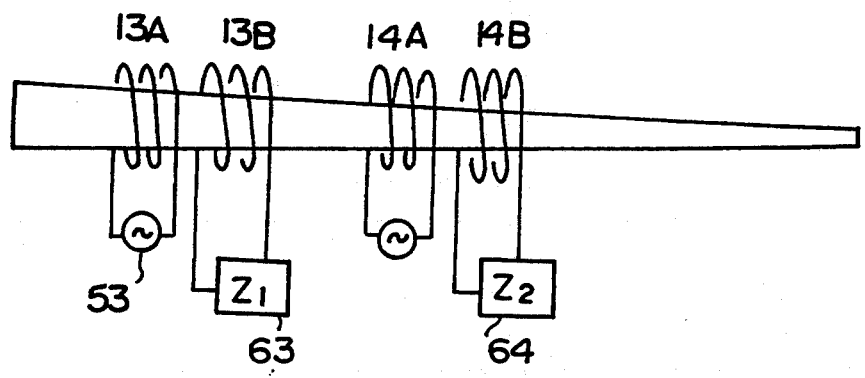
FIG. 10 is a schematic diagram illustrating a first operating mode of a second embodiment of the present invention.

In the second embodiment, the first coil 13, second coil 14 and third coil 15 comprise respective pairs of coils 13A, 13B, 14A, 14B and 15A, 15B as shown in FIG. 10 and FIG. 12. The respective pairs of coils comprise excitation coils 13A, 14A and 15A connected to an alternating current power source, and detection coils 13B, 14B, and 15B for detecting any fluctuation in an induced EMF which is produced as a result of applying an alternating current to the excitation coils 13A, 14A and 15A.

Initially, a first operating mode according to the second embodiment wherein only the first coil 13, and second coil 14 are used will be described with reference to FIG. 10 and FIG. 11.

According to a second embodiment of the present invention, the self comparison/standard comparison switch 24 is switched to the self comparison side, then the alternating current is applied to the first and second excitation coils 13A and 14A, and a bridge circuit 173 is formed to detect a change in induced electromotive force generated in the first and second detection coils 13B and 14B. On the other hand, if the self comparison/standard comparison switch 24 is switched to the standard comparison side, then the alternating current is applied to the second and third excitation coils 14A and 15A and a bridge circuit 175 is formed to detect a change in induced electromotive force generated in the second and third detection coils 14A and 15B.

That is to say, an alternating current power source 53 is connected to the first excitation coil 13A and the second excitation coil 14A. An impedance 63 is then connected to the first detection coil 13B and an impedance 64 is connected to the second detection coil 14B.

Figure 11:
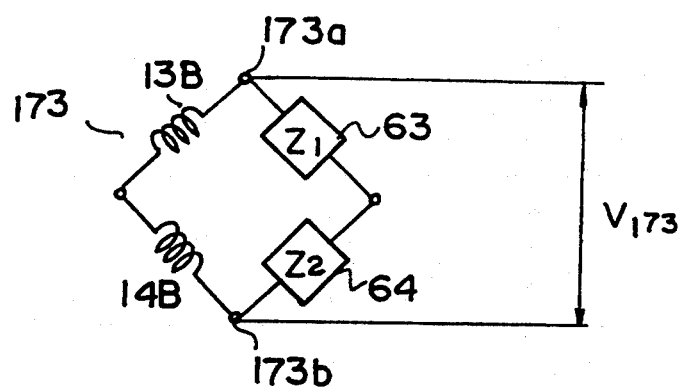
FIG. 11 is a bridge circuit diagram for the first operating mode of the second embodiment.

As shown in FIG. 11, the first detection coil 13B and the second detection coil 14B are arranged to make up a bridge circuit 173 so as to detect any fluctuation in an induced EMF which is produced as a result of applying an alternating current to the first excitation coil 13A and the second excitation coil 14A. With the insertion of a defective portion of a test object into the second detection coil 14B, the balance of the bridge circuit 173 collapses giving an output voltage $V_{173}$ between terminals 173a and 173b, corresponding to the change in coil impedance of the second detection coil 14B due to the defect.

That is to say, whereas in the first embodiment the excitation coils 13A, 14A and detection coils 13B, 14B are combined as one in the first coil 13 and the second coil 14 respectively, in the second embodiment, these are each provided separately. Moreover, in the second embodiment, the detection coil 13B, 14B may be connected facing an opposite direction instead of being connected to make up the bridge circuit 173.

The output conditions of the output voltage $V_{173}$ when the apparatus 1 is used in the second embodiment in the first operating mode are the same as the previously discussed output conditions of output voltage $V_{73}$ and flaw 39 location for the standard object 35, and hence, a description of these conditions is omitted.

Next, a second operating mode according to the second embodiment wherein only the second coil 14, and third coil 15 are used, will be described with reference to FIG. 12 and FIG. 13. That is to say, the alternating current power source 55 is connected to the second excitation coil 14A and the third excitation coil 15A. An impedance 64 is then connected to the second detection coil 14B and an impedance 65 is connected to the third detection coil 15B.

As shown in FIG. 13, the second detection coil 14B and the third detection coil 15B are arranged to make up a bridge circuit 175 so as to detect any fluctuation in an induced EMF which is produced as a result of applying an alternating current to the second excitation coil 14A and the third excitation coil 15A. With the insertion of a defective portion of a test object into the third detection coil 15B, the balance of the bridge circuit 175 collapses giving an output voltage $V_{175}$ between terminals 175a and 175b, corresponding to the change in coil impedance of the third detection coil 15B due to the defect.

That is to say, whereas in the first embodiment the excitation coils 14A, 15A and detection coils 14B, 15B are combined as one in the second coil 14 and the third coil 15 respectively, in the second embodiment, these are each provided separately.

In the second operating mode, the standard object 35 is inserted into the second coil 14, and the test object 31, as a trial object, is inserted into the third coil 15. The test object 31 is used for inspection to determine the extent of defects such as flaw 37 compared to the standard object 35.

The output conditions of the output voltage $V_{175}$ when the inspection apparatus is used in the second embodiment in the second operating mode are the same as the previously discussed output conditions of output voltage $V_{75}$ and flaw 39 location for the standard object 35, and hence, a description of these conditions is omitted.

Accordingly, with the second operating mode as described above, the test object 31 can be inspected to determine the extent of defects such as a flaw 37 compared to the standard object 35. The second operating mode thus functions in effect according to the second embodiment of the present invention.

Operation of the apparatus is started by pressing an inspection start switch 25 (FIG. 2). At first the switch 24 is switched to "self comparison", and the standard object 35 is inspected to see the extent of defects such as flaw 39.

The standard object 35 is positioned so as to pass through the first excitation coil 13A and the first detection coil 13B, and the second excitation coil 14A and the second detection coil 14B. The alternating current power source 53 is connected to the first excitation coil 13A and the second excitation coil 14A, and the output voltage $V_{173}$ from the bridge circuit 173 is detected.

That is to say, the bridge output voltage detection device comprises the bridge circuit 173 and the bridge circuit 175.

If there are practically no flaws in the standard object 35, then the output voltage $V_{173}$ is practically zero. Consequently, as well as being able to pre-check the degree of flaws, it is possible to select a standard object 35 with practically no flaws.

The switch 24 is then switched to "standard comparison" and the test object 31 is scanned as described in the following.

First is a description, with reference to FIG. 14 to 21, of the function wherein the apparatus 1 detects whether or not there are flaws in the test object 31, and judges whether or not the test object 31 will pass as a manufactured product.

In the beforementioned first embodiment, the second coil 14 and third coil 15 are scanned relative to the test object 31, and the output voltage $V_{75}$ is detected by means of the output voltmeter 85.

In the second embodiment, the second detection coil 14B and the third detection coil 15B are scanned relative to the test object 31, and the output voltage $V_{175}$ detected.

Since the conditions of the output voltage related to defect occurrence are the same for both the first and second embodiments, the following explanation will be given with respect to the output voltage $V_{75}$.

This voltage $V_{75}$ is input to the control unit 26 (FIG. 2) housing a microcomputer therein, various corrections made for defect detection, and the torsional breakage torque is determined.

As follows is a description using a flow chart, of the various computation routines carried out by the control unit 26 for inspection of a golf club shaft. In the following description, the axial direction from the tip ends of the test object 31 and the standard object 35 to their respective rear ends is taken as the X axis.

Figure 14:
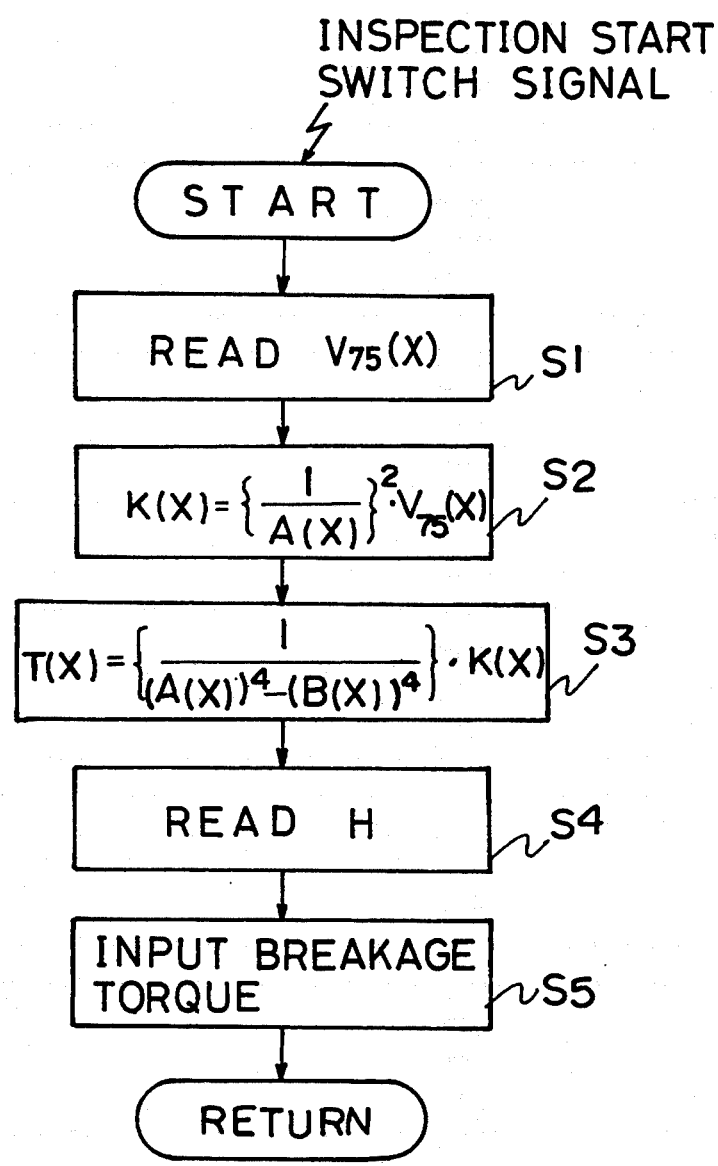
FIG. 14 is a flow chart illustrating an inspection strength determining routine for the above embodiments.

First, a description of the detection strength determining routine for determining the detection strength H is given with reference to FIG. 14. This routine is used in a threshold value determining routine for determining the threshold value VSL used to judge if the product is good or bad. The detection strength determining routine is carried out with respect to the single test object, on input of the inspection start switch signal.

In step 1 (S1 in the figure, with subsequent steps indicated by S), the output voltage $V_{75}(x)$ obtained by the beforementioned scanning, is read for the various points along the X axis of the test object 31. A typical output is shown in FIG. 15 for an article with a large number of defects.

Figure 15:
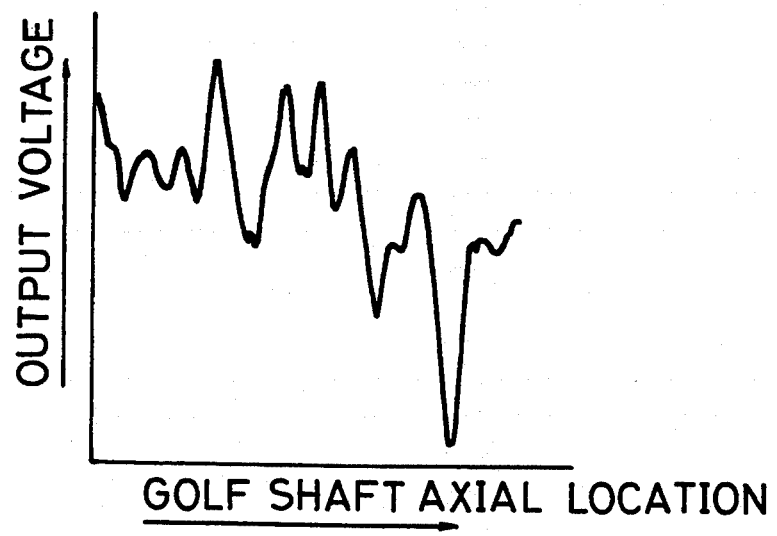
FIG. 15 is a graph illustrating the relationship between detection location and output voltage for the above embodiments.
Figure 16:
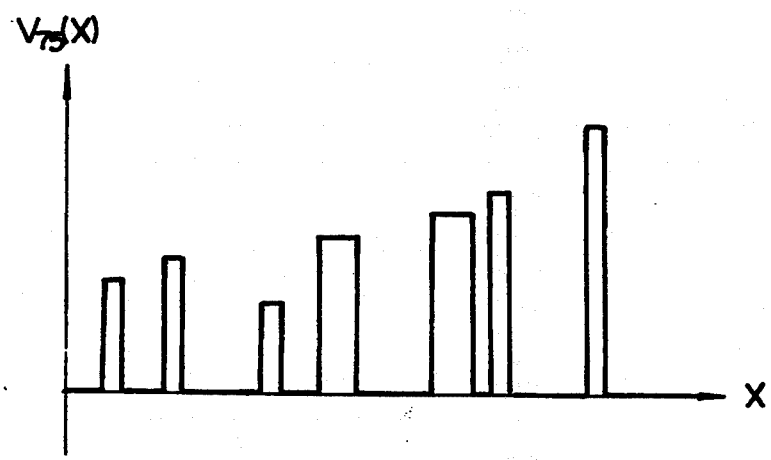
FIG. 16 is a graph illustrating fluctuation values of the output voltage detected in the above embodiments.

The output voltage $V_{75}(x)$ is for a direct current, and the output shown in FIG. 15 is for a combination of outputs corresponding to FIG. 9C1 to FIG. 9C3. The output signal is digitized as shown in FIG. 16 (digitized output for only a few flaws is shown for simplicity) for input to the control unit 26.

In step 2, the voltage $V_{75}(x)$ is corrected depending on the cross sectional area ratio of the test object relating to the cross sectional area of the coil.

Since detection sensitivity is lowered when the cross sectional area of the test object 31 relative to the cross sectional area of the second coil 14 is small, a taper correction value $K(x) = V_{75}(x) \times [1/(A(x))^2]$ is computed by integration of the inverse square of the outer diameter $A(x)$ into the output voltage $V_{75}(x)$.

In computing the correction value, the inverse square of the outer diameter $A(x)$ is integrated. However, instead of the outer diameter $A(x)$, the inverse square of the inner diameter $B(x)$ may be integrated. The taper correction value may thus be given by $K(x) = V_{75}(x) \times [1/A(x)]^2$.

In step 3, the output voltage $V_{75}(x)$ is corrected depending on the flaw size and the diameter at the location of the flaw.

The influence is larger for the same size flaw, at locations on the test object 31 where the diameter is small, and reduces with increase in diameter. The taper correction value $K(x)$ computed in step 2 is thus corrected according to the following equation, to give diameter correction values $T(x)$ in step 3 such as shown in FIG. 17.

$$T(x) = K(x) \times [1/\{(A(x))^4 - (B(x))^4\}]$$

Figure 17:
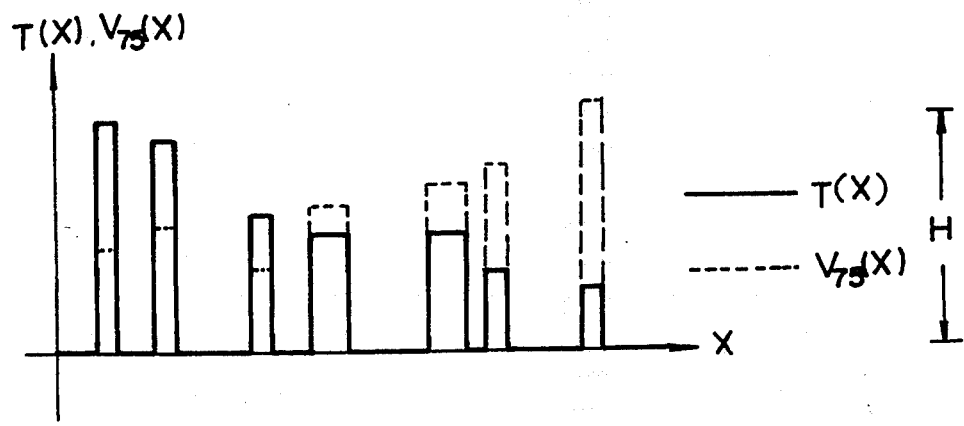
FIG. 17 ms a diagram illustrating output voltage correction values and detection strength H for the above embodiments.

In step 4, the absolute value of the maximum peak value of the diameter correction value $T(x)$ is obtained to give detection strength H (see FIG. 17).

On completion of step 4, the test object 31 is removed from the inspection apparatus and placed in the breakage torque measuring apparatus (not shown in the drawings).

In step 5 the breakage torque $T_{BR}$ for the test object 31 measured with the breakage torque measuring apparatus is input.

The relationship between the detection strength H and the breakage torque $T_{BR}$ for the test object 31 can be obtained by means of the above described detection strength determining routine. This routine is carried out for a number of test objects 31 having the same laminated construction, shape, and dimensions, to obtain a graph line 41 such as shown in FIG. 18, which gives the relationship between the various detection strengths H and breakage torques $T_{BR}$.

Figure 19:
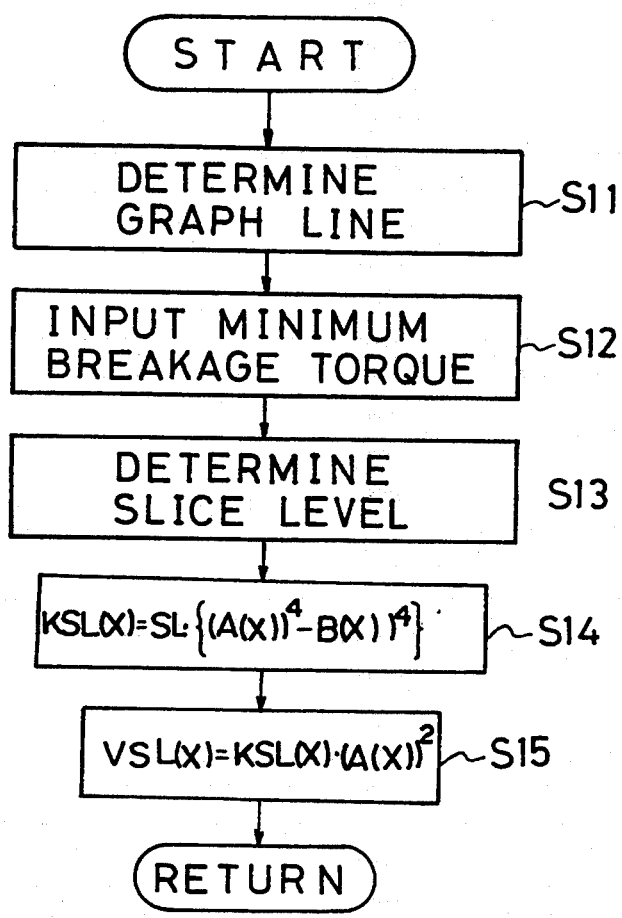
FIG. 19 is a flow chart illustrating a threshold value determining routine for the above embodiments.

As follows is a description with reference to FIG. 19, of a threshold value determining routine for determining the threshold value VSL from the relationship between detection strength H and the breakage torque $T_{BR}$.

Figure 18:
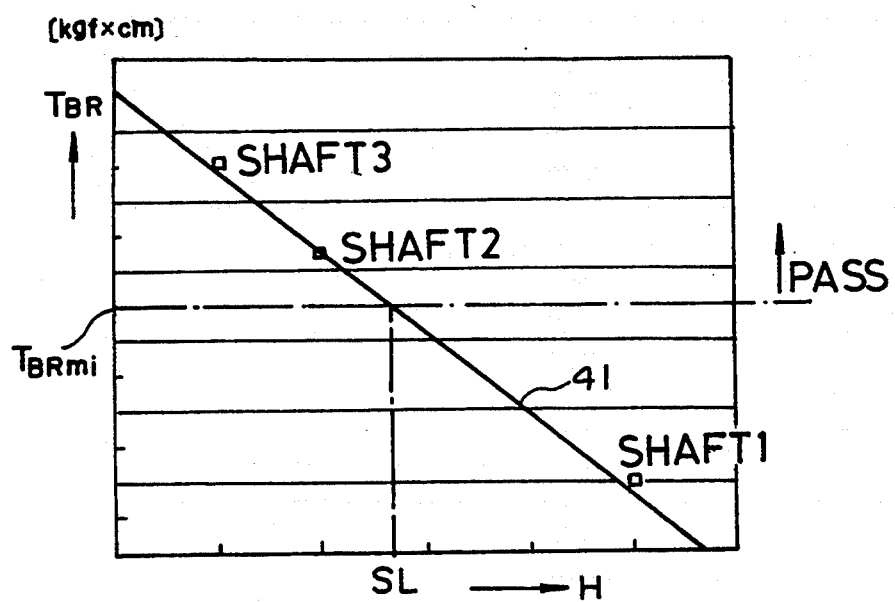
FIG. 18 ms a graph illustrating the relationship between a plurality of detected strengths H and breakage torque $T_{BR}$ for the above embodiments.

In step 11, data from the graph line 41 of FIG. 18 is input.

In step 12, the minimum breakage torque $T_{BRmi}$ being the minimum allowable value for the breakage torque $T_{BR}$ is input.

In step 13, a slice level SL is read from the graph line 41 as the detection strength H corresponding to the minimum breakage torque $T_{BRmi}$.

In step 14, the read slice level SL is corrected depending on the flaw size and the diameter at the location of the flaw.

That is to say, as with step 5, the slice level SL is corrected according to the following equation to give a correction value $KSL(x)$.

$$KSL(x) = SL \times \{(A(x))^4 - (B(x))^4\}$$

In step 15 the output correction value $KSL(x)$ is corrected depending on the cross sectional area ratio of the test object relating to the cross sectional area of the coil.

That is to say, as with step 4, the correction value KSL(x) is corrected according to the following equation to give a threshold value VSL.

$$VSL(x) = KSL(x) \times (A(x))^2$$

As with step 4, $VSL(x) = KSL(x) \times (B(x))^2$ is also possible.

Figure 20:
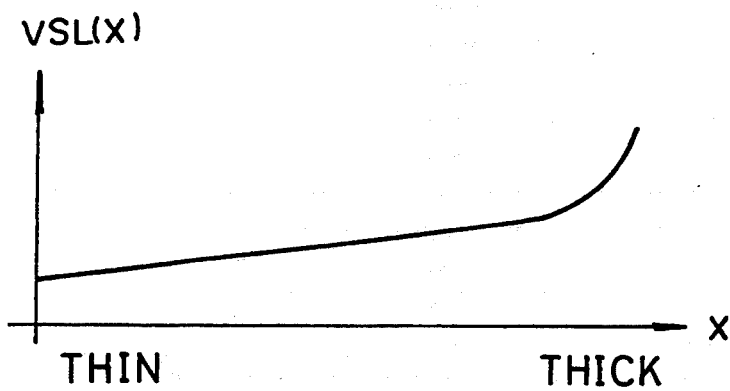
FIG. 20 is a graph illustrating change in threshold value $VSL(x)$ with distance along the x axis for the above embodiments.

By means of the above described detection strength determining routine and threshold value determining routine, threshold values VSL(x) are determined for location along the axis of test object 31 (X-axis) as shown in FIG. 20.

Step 2 and step 15 described above function as comparative sensitivity correction devices, and step 3 and step 14 function as sectional area ratio correction devices.

Figure 21:
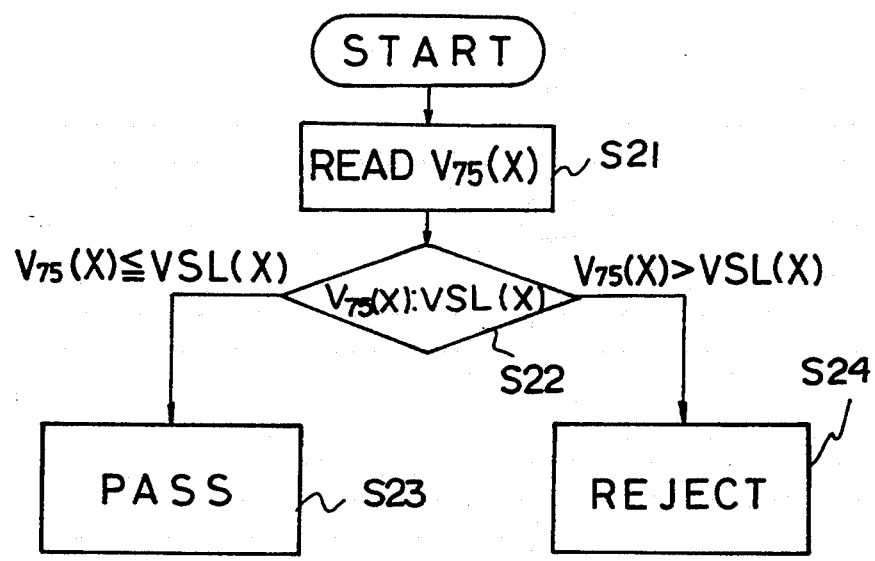
FIG. 21 is a flow chart illustrating a flaw detection routine for the above embodiments.

As follows is a description with reference to FIG. 21, of a defect detection routine for detecting defects in the test object 31 on the basis of the threshold value VSL(x) obtained from the threshold value determining routine.

In step 21, as with step 1, the output voltage $V_{75}(x)$ obtained by the beforementioned scanning, is read for the various points along the X axis of the test object 31.

In step 22, the voltage value $V_{75}(x)$ and the threshold value VSL(x) are compared for various locations.

Figure 22:
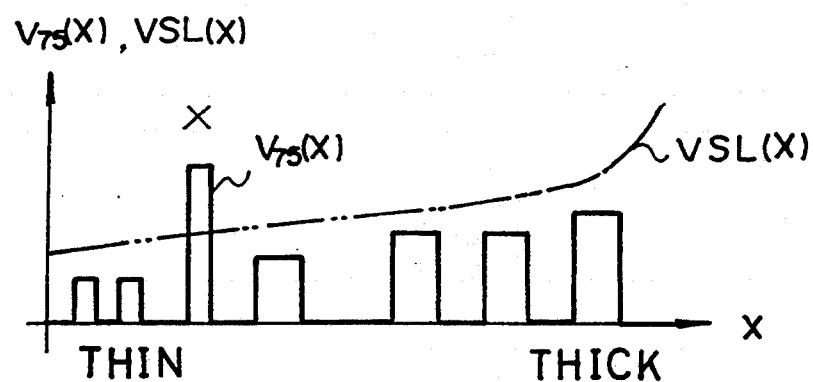
FIG. 22 is a graph illustrating the relationship between output voltage fluctuation values and threshold value VSL in the above embodiments (in the case of defective products).

If the voltage value $V_{75}(x)$ does not exceed the threshold value VSL(x), control proceeds to step 23 to light the acceptance lamp 28 with a pass for test object 31 and inspection is completed. However, as shown in FIG. 22, if there is a point where $V_{75}(x)$ exceeds VSL(x) (shown by X in FIG. 22), control proceeds to step 24, a fail lamp 29 comes on, and inspection ceases with a fail for the test object 31.

As described above, with the present embodiments, the voltage value $V_{75}$ which depends on whether or not a detectable defect exists at the various points along the X-axis of test object 31, is compared with the threshold value VSL(x) for the standard object 35. Hence, even with a continuous defect, an accurate assessment of the defect condition is possible. It is thus possible to appropriately judge whether or not a flaw is a defect, resulting in an improvement in the accuracy of detecting defects in the test object 31.

Moreover, the voltage $V_{75}(x)$ is corrected depending on diameter, and the diameter at the location of the flaw. Hence, even if the same flaw exists at different locations in the test object 31, a quantitative assessment of the influence of the flaw on the test object 31 is possible, resulting in an improvement in defect detection accuracy.

Furthermore, the threshold value VSL(x) is obtained by correcting the slice level SL depending on the cross sectional area ratio, and on the diameter, at the location of the flaw. Hence, since a comparison is made between the threshold value and the voltage value $V_{75}(x)$ obtained from the test object 31, the time taken for assessment can be shortened compared to the case when the voltage value $V_{75}(x)$ is corrected.

In addition, since it is possible to reliably determine the location of the defect, then defect cases can be confirmed.

As follows is a description, with reference to FIG. 23 to FIG. 26 for the case when the apparatus 1 functions to determining the permissible breakage torque of the test object 31.

At first, a graph line 45 (see FIG. 23) showing the relationship between the detection strength H and the breakage torque $T_{BR}$ is obtained by means of the detection strength determining routine of FIG. 14. Predetermined threshold values are then obtained.

Figure 24:
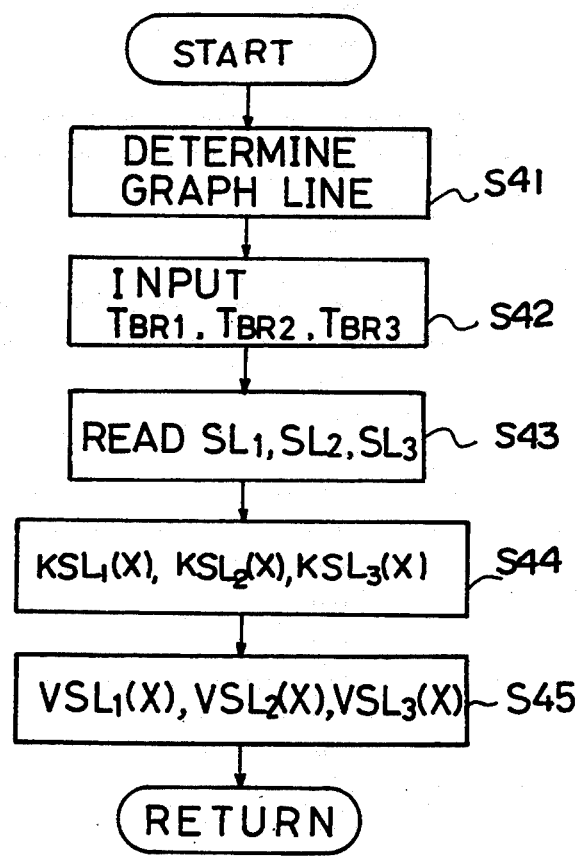
FIG. 24 is a flow chart illustrating a threshold value determining routine for the above embodiments.

As follows is a description with reference to FIG. 24, of a predetermined threshold value determining routine for determining a predetermined threshold value corresponding to a predetermined breakage torque obtained from the relationship between detection strength H and the breakage torque $T_{BR}$ obtained from the detection strength determining routine.

Figure 23:
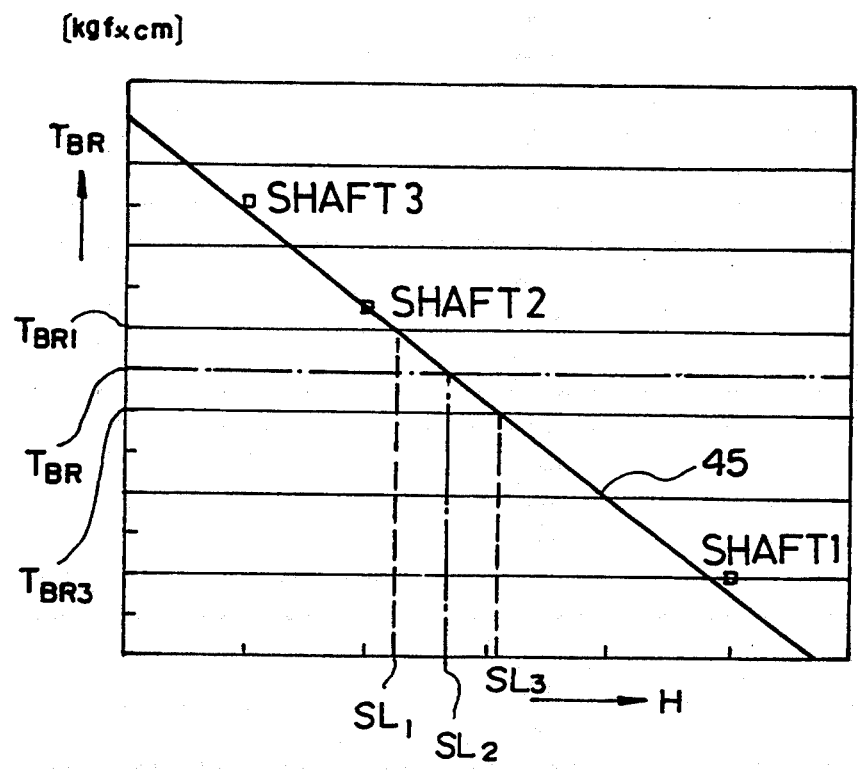
FIG. 23 is a graph illustrating the relationship between several output strengths H and breakage torque $T_{BR}$ for the above embodiments.

In step 41, data from the graph line 45 of FIG. 23 is input.

In step 42, the predetermined breakage torques $T_{BR1}$, $T_{BR2}$ and $T_{BR3}$ are input.

In step 43, the slice levels $SL_1$, $SL_2$ and $SL_3$ are read from the graph line 45 as detection strengths H corresponding to the predetermined breakage torques $T_{BR1}$, $T_{BR2}$ and $T_{BR3}$.

In step 44, the read slice level $SL_1$, $SL_2$ and $SL_3$ correction values $KSL_1(x)$, $KSL_2(x)$ and $KSL_3(x)$ for the influence of the flaw size and the diameter at the location of the flaw are obtained in a similar manner to that in the beforementioned threshold value determining routine of step 14.

In step 45, the correction values $VSL_1(x)$, $VSL_2(x)$ and $VSL_3(x)$ for the cross sectional area ratio of the test object relating to the cross sectional area of the coil corresponding to the correction values $KSL_1(x)$, $KSL_2(x)$ and $KSL_3(x)$ from step 4 are obtained in a similar manner to that of the beforementioned threshold value determining routine of step 15.

Figure 25:
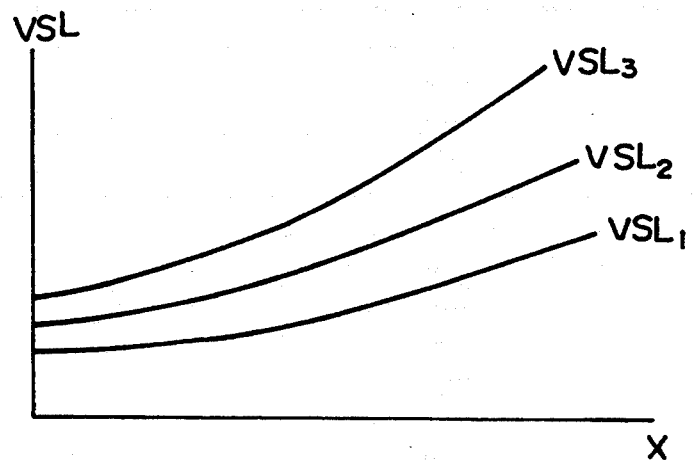
FIG. 25 is a graph illustrating change in threshold value $VSL_1(x)$, $VSL_2(x)$ and $VSL_3(x)$ with distance along the x axis for the above embodiments.

By means of the above described predetermined threshold value determining routine, predetermined threshold values $VSL_1(x)$, $VSL_2(x)$ and $VSL_3(x)$ are then determined for location along the axis (X-axis) as shown in FIG. 25.

Figure 26:
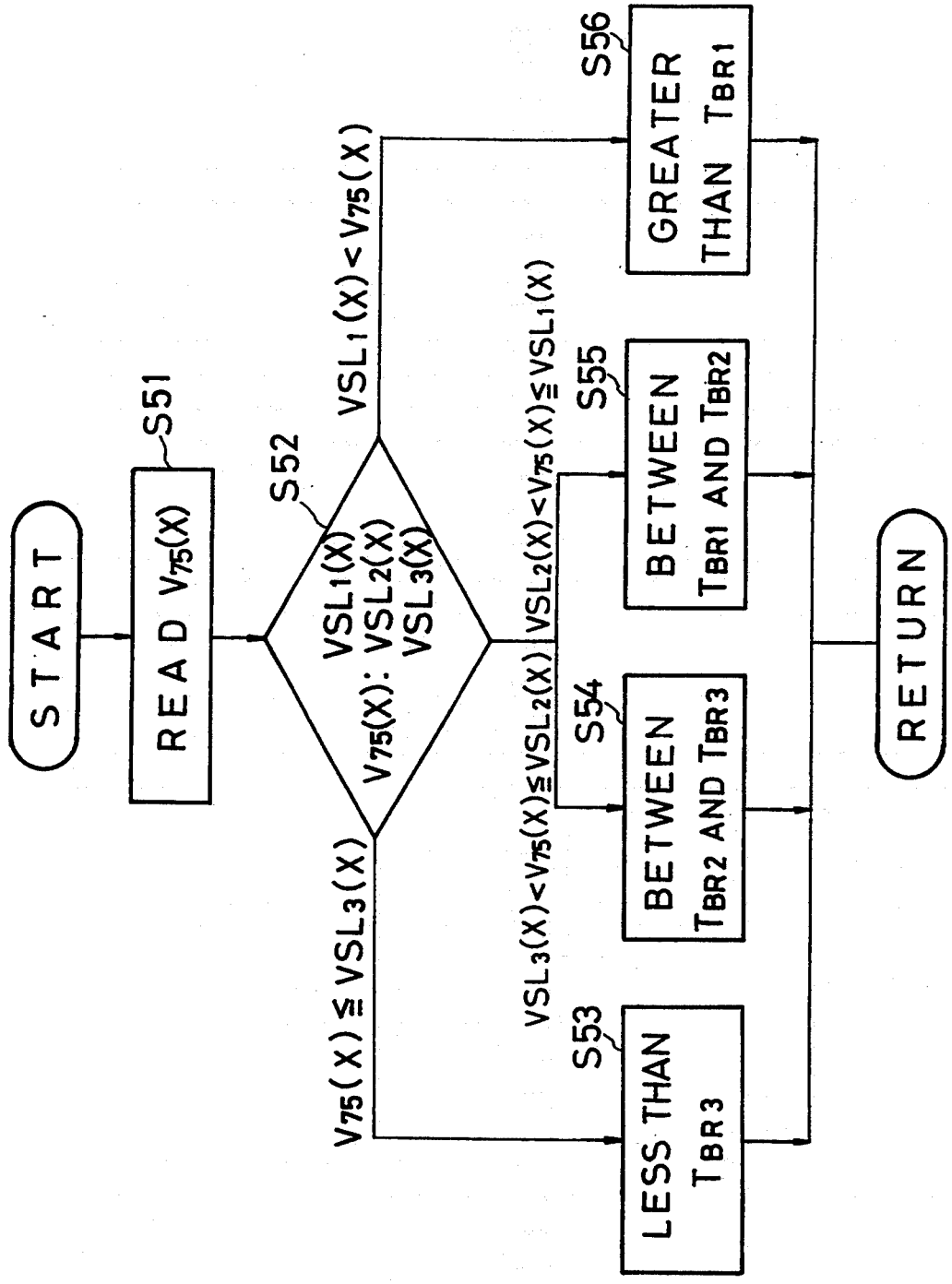
FIG. 26 is a flow chart illustrating a torsional breakage torque determining routine for the above embodiments.
Figure 27:
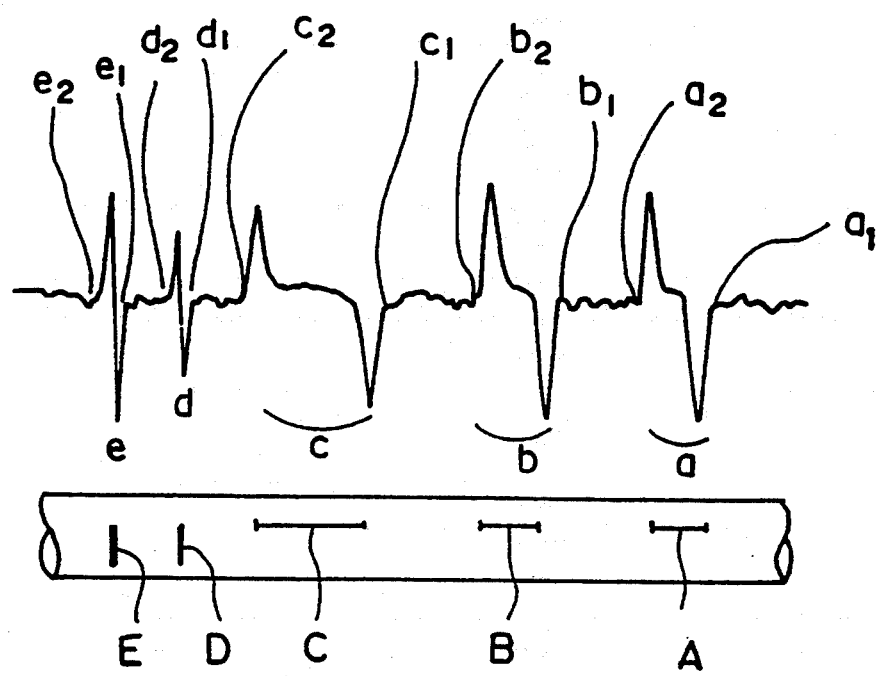
FIG. 27 is a diagram illustrating a relationship between defects and output voltage for the above embodiments.

As follows is a description, with reference to FIG. 26 of a breakage torque prediction routine for determining the permissible breakage torque of the test object 31 on the basis of the threshold value VSL(x) obtained from the threshold value determining routine.

In step 51, as with step 1, the output voltage $V_{75}(x)$ obtained by the beforementioned scanning, is read for the various points along the X axis of the test object 31.

In step 52, the voltage value $V_{75}(x)$ and the threshold values $VSL_1(x)$, $VSL_2(x)$, and $VSL_3(x)$ are compared for various locations. If there is a point where the voltage value $V_{75}(x)$ exceeds the threshold values $VSL_1(x)$, $VSL_2(x)$, and $VSL_3(x)$, then the test object 31 can be predicted to break at the predetermined breakage torque at that location, and the breakage torque of the test object 31 can thus be judged.

That is to say, if in step 52, $V_{75}(x)$ is judged less than or equal to $VSL_3(x)$, then control proceeds to step 53, and the test object 31 breakage torque is judged to be less than $TBR_3$.

If in step 52, $VSL_3(x)$ is judged less than $V_{75}(x)$ and $V_{75}(x)$ is judged less than or equal to $VSL_2(x)$, then control proceeds to step 54, and the test object 31 breakage torque is judged to be between $TBR_2$ and $TBR_3$.

If in step 52, $VSL_2(x)$ is judged less than $V_{75}(x)$ and $V_{75}(x)$ is judged less than or equal to $VSL_1(x)$, then control proceeds to step 55, and the test object 31 breakage torque is judged to be between $T_{BR1}$ and $T_{BR2}$.

If, however, in step 52, $VSL_1(x)$ is judged less than $V_{75}(x)$, then control proceeds to step 56, and the test object 31 breakage torque is judged to be greater than $T_{BR1}$.

That is to say, the breakage torque determination routine functions as torsional breakage torque determination device.

As described above, with the present embodiments, it is possible to instantaneously judge the breakage torque of the test object 31 at various points along the X-axis. For example, it is possible to promptly judge the strength of the test object 31, and to instantaneously judge without any damage, whether or not the breakage torque of the test object exceeds or is below the pass standard.

Moreover, the voltage $V_{75}(x)$ is corrected depending on the cross sectional area ratio of the test object relating to the cross sectional area of the coil, and on the flaw size and the diameter at the location of the flaw. Hence, even if the same flaw exists at different locations in the test object 31, a quantitative assessment of the influence of the flaw on the test object 31 is possible, resulting in an improvement in accuracy when determining the torsional breakage torque.

Furthermore, since it is possible to reliably determine the location of the defect, then defect cases can be confirmed.

Also, since the quality of the product may be determined quantitatively, the judgment system related to the quality judgment can be improved with the result that quality control of the products may be improved.

We claim:

1. A method for the nondestructive determination of torsional breakage torque of tubular carbon fiber reinforced composite materials (CFRC) comprising the steps of:

inserting a tubular CFRC material test object and a standard object into respective single coils or respective double coils, said standard object having the same external diametric dimensions as said test object and having a previously verified degree of flaws;

passing a predetermined alternating current through each of said single coils or one coil of each of said double coils to generate eddy currents in said standard object and said test object;

moving said coils relative to said standard object and said test object in an axial direction to scan said standard object and said test object;

detecting an output fluctuation of eddy currents due to a flaw as an output voltage from a bridge circuit which includes each of said single coils or the other coil of each of said double coils;

wherein said test object and said standard object are formed from tapered tubular carbon fiber reinforced composite material which has been wound with carbon fiber at a predetermined angle with respect to the axial direction;

said output voltage is corrected on the basis of the diametric dimension at the scanning location of said test object; and the torsional breakage torque of said test object is quantitatively determined for each inspection location on the basis of the corrected output.

2. An apparatus for the nondestructive determination of torsional breakage torque of tubular carbon fiber reinforced composite materials (CFRC) comprising:

a single standard object coil or a double standard object coil for accommodating a standard object which has the same external diametric dimensions as a tubular CFRC material test object and which has a previously verified degree of flaws;

a single test object coil or a double test object coil for accommodating said test object;

an alternating current application means for passing an alternating current through each of said single standard object and test object coils or one coil of each of said double standard object and test object coils;

a scanning means for moving said coils, said standard object, and said test object relative to each other in an axial direction;

a bridge circuit including each of said standard object and single test object coils or the other coil of each of said double standard object and test object coils;

a bridge output voltage detection means for detecting fluctuation of eddy currents generated in said standard object and said test object by said alternating current application means due to a flaw;

a correction means for correcting said bridge output voltage on the basis of the diametric dimension at the scanning location of said test object and said standard object which are formed from a tapered tubular carbon fiber reinforced composite material wound with carbon fiber at a predetermined angle with respect to the axial direction; and a determination means for quantitatively determining the torsional breakage torque of said test object on the basis of the corrected output.

3. An apparatus for the nondestructive determination of torsional breakage torque of tubular carbon fiber reinforced composite materials as claimed in claim 2, wherein said correction means comprises a cross sectional area correction means which corrects the output of said bridge output voltage detection means on the basis of the cross sectional area of the test object relative to the cross sectional area of the coil.

4. An apparatus for the nondestructive determination of torsional breakage torque of tubular carbon fiber reinforced composite materials as claimed in claim 2, wherein said correction means comprises a diameter correction means which corrects the output from said bridge output voltage detection means depending on the flaw size and the diameter of the test object at the inspection location of the flaw.

5. An apparatus for the nondestructive determination of torsional breakage torque of tubular carbon fiber reinforced composite materials as claimed in claim 3, wherein said correction means further comprises a diameter correction means which corrects the output from said bridge output voltage detection means depending on the flaw size and the diameter of the test object at the inspection location of the flaw.

6. An apparatus for the nondestructive determination of torsional breakage torque of tubular carbon fiber reinforced composite materials as claimed in claim 2, wherein said tubular carbon fiber reinforced composite material is a golf club shaft.

7. An apparatus for the nondestructive determination of torsional breakage torque of tubular carbon fiber reinforced composite materials as claimed in claim 2, wherein said scanning means comprises a ball screw driven by a motor.

8. An apparatus for the nondestructive determination of torsional breakage torque of tubular carbon fiber reinforced composite materials as claimed in claim 2, wherein said test object coil and said standard object coil are each a single coil.

9. An apparatus for the nondestructive determination of torsional breakage torque of tubular carbon fiber reinforced composite materials as claimed in claim 2, wherein said alternating current application means comprises an alternating current source.

10. An apparatus for the nondestructive determination of torsional breakage torque of tubular carbon fiber reinforced composite materials as claimed in claim 2, wherein a test object is inserted into said test object coil and a standard object is inserted into said standard object coil and said bridge circuit comprises said standard object coil and said test object coil.

11. An apparatus for the nondestructive determination of torsional breakage torque of tubular carbon fiber reinforced composite materials as claimed in claim 2, wherein each of said test object coil and said standard object coil comprises a plurality of coils.

12. An apparatus for the nondestructive determination of torsional breakage torque of tubular carbon fiber reinforced composite materials as claimed in claim 2, wherein an influence exerted by defects at different locations in said test object is quantitatively determined by said determining means.

13. An apparatus for the nondestructive determination of torsional breakage torque of tubular carbon fiber reinforced composite materials as claimed in claim 2, further comprising a standard object inspection means for inspecting said standard object prior to inspection of said test object wherein only said standard object is inserted into said standard coil and a bridge circuit comprises only said standard object coil.

* * * * *